US012099832B2

(12) United States Patent
Griffor et al.

(10) Patent No.: US 12,099,832 B2
(45) Date of Patent: Sep. 24, 2024

(54) INTERNET OF THINGS (IOT) CAPABILITY PLATFORM

(71) Applicants: Edward Ronald Griffor, Grosse Pointe Park, MI (US); Ahmed Lbath, Saint-Priest (FR)

(72) Inventors: Edward Ronald Griffor, Grosse Pointe Park, MI (US); Ahmed Lbath, Saint-Priest (FR)

(73) Assignee: UNIVERSITE DE GRENOBLE ALPES, Grenoble (FR)

( * ) Notice: Subject to any disclaimer, the term of this patent is extended or adjusted under 35 U.S.C. 154(b) by 510 days.

(21) Appl. No.: 17/520,221

(22) Filed: Nov. 5, 2021

(65) Prior Publication Data

US 2022/0148741 A1   May 12, 2022

Related U.S. Application Data

(60) Provisional application No. 63/110,610, filed on Nov. 6, 2020.

(51) Int. Cl.
| | | |
|---|---|---|
| *G06F 8/70* | (2018.01) | |
| *G01S 19/01* | (2010.01) | |
| *G06N 20/00* | (2019.01) | |
| *G16H 40/67* | (2018.01) | |
| *G16H 50/80* | (2018.01) | |
| *G16Y 10/60* | (2020.01) | |
| *G16Y 10/75* | (2020.01) | |

(52) U.S. Cl.
CPC ............... *G06F 8/70* (2013.01); *G01S 19/01* (2013.01); *G06N 20/00* (2019.01); *G16H 40/67* (2018.01); *G16H 50/80* (2018.01); *G16Y 10/60* (2020.01); *G16Y 10/75* (2020.01)

(58) Field of Classification Search
USPC .................................. 717/106–113, 120–123
See application file for complete search history.

(56) References Cited

U.S. PATENT DOCUMENTS

| 11,025,501 | B1 * | 6/2021 | Iyer .................... H04W 28/0231 |
| 11,888,716 | B1 * | 1/2024 | Lloyd ...................... H04L 43/16 |
| 2019/0297078 | A1 * | 9/2019 | Davis, III ............ H04L 63/0876 |
| 2020/0145493 | A1 * | 5/2020 | Wang ....................... H04L 67/56 |
| 2020/0245148 | A1 * | 7/2020 | Patil ..................... H04L 12/4641 |
| 2020/0327371 | A1 * | 10/2020 | Sharma .................... G06N 3/08 |
| 2022/0067669 | A1 * | 3/2022 | Griffin .................. G16Y 40/20 |

* cited by examiner

*Primary Examiner* — Qing Chen
(74) *Attorney, Agent, or Firm* — Fitch, Even, Tabin & Flannery, LLP

(57) ABSTRACT

A method for the Internet of Things refers to objects to exchange information over the Internet. An IoT system refers to one or more IoT objects that exchange information and, through those exchanges, produces information that meets an objective or purpose, including the actuation of mechanical systems. An IoT system that refers to a single IoT object may also be referred to as an IoT device. The capability of an IoT systems refers to the information produced by the system to achieve its objective or purpose. The present embodiments may be implemented by computer software on a networked digital computer or a dedicated microprocessor, connected to a digital network. The embodiments create descriptions of IoT systems and provides a means of searching over these descriptions for those satisfying search criteria and a means of composing two or more descriptions to form a description of the composition of IoT systems.

1 Claim, 7 Drawing Sheets

INTERNET OF THINGS (IOT) CAPABILITY PLATFORM

CROSS-REFERENCE TO RELATED APPLICATION

This application is a U.S. Non-provisional application and claims priority from U.S. Provisional Application No. 63/110,610, filed Nov. 6, 2020, which is hereby incorporated herein by reference in its entirety for all purposes.

FIELD

The present embodiments relate generally to information and communication technology adapted for the Internet of Things and, more specifically to inter-networking of physical objects ("things") that embed technology enabling the things to sense and collect information from their internal state or their external environment, wherein the information is processed by the things or by other devices, e.g. servers, to be output to the things, to other things or to other devices, and enabling these things to be connected to the Internet either directly or indirectly.

BACKGROUND

Monitoring and maintaining the quality of Internet of Things ("IoT") information and capabilities, of varying types and formats including location and timing information and temperature and the like, is a major concern for both government and private sector organizations. If an organization is not able to identify, gather, manage, and control the dissemination of its information, many potential failures of organizational processes or systems may occur, including system failures, process failures or violations of organizational policies, including unauthorized disclosures of information. The consequences of such failures may cause an organization to lose market share, persist in less than optimal practices, lose trade secrets, or, in the case of government organizations, may actually lead to exposing individuals and assets to hazards, including security hazards.

Organizations often have written policies to govern the management of the information produced by its technologies, including information produced by sensors and other IoT systems. However, the implementation of these policies is partially or wholly manual and is left up to individual employees of an organization using disparate computing systems. By way of a non-limiting example, an organization may have sensors or monitoring devices designed to ensure the comfort and efficiency of its facilities through measurement of temperature, air quality, humidity, lighting and the like. Nevertheless, the level of comfort of individuals varies, and it is left up to employees to actually modify the settings of these devices. Whenever an information management policy is left to human beings for implementation, a potential source of error or failure exists where the policy may not be followed, or at least may not be followed in every situation and, further, that information may not be available to everyone that may derive value from it.

Network device scanners, with network performance monitoring, are in use to monitor, discover, map, and/or scan for network devices. These engines are networking controller resident programs that identify and index any node of a network that possesses network communication capability and possesses a connection to that network, including sensors, other computing devices or a client computer that has connections to such devices. Examples of such network device scanners include those sold under the tradename WIRESHARK™, OPENVAS™, and SPYSE™.

With such network device scanners, a user may scan for network devices, assess network performance and generate reports that capture which devices are available on the network and how well network communications are currently functioning between that device and other devices currently connected to that network. Such network device scanner can identify the devices on the network and gather and report on networking relevant information, tags or meta-tags of the device, or the like. Results of the scan may then be provided to the user of such network device scanners. In this way, a user is able to obtain easy access to information as to which devices are on their computer network and assess the speed of communications on that network, and the like.

Network scanning and monitoring belong to a category of network management tools and are focused on the quality of communications, or even simply managing, rather than on the quality of the information that is exchanged between IoT systems.

Despite these advances in the art, further improvements are desired.

SUMMARY

The present embodiments relate generally to information and communication technology adapted for the Internet of Things and, more specifically to inter-networking of physical objects ("things") that embed technology enabling the things to sense and collect information from their internal state or their external environment, wherein the information is processed by the things or by other devices, e.g. servers, to be output to the things, to other things or to other devices, and enabling these things to be connected to the Internet, either directly or indirectly, and enabling these things to be regarded as capabilities and combined in novel ways based on the present embodiments characterization of the qualities of the information they produce and exchange.

In one illustrative embodiment, the present embodiments provide a method for identifying, storing, searching and combining IoT systems capabilities to produce business value, such as managing building and facility environment management and data monetization. In one method of the present embodiments, an IoT search rule is one or more specifications, and a specification is one or more constraints on IoT system information variables that represent some or all of the characteristic information of an IoT system. The remaining variables of an IoT search rule are referred to as the IoT system information parameters. In one illustrative embodiment, the present embodiments provide a method for expressing constraints on the characteristic information of IoT capabilities to produce what is referred to as a specification of IoT capabilities. By a weakening of a constraint in a specification is meant, one that implies logically the constraint, such as allowing one or more characteristic information in the constraint to vary over a larger set of values, and obtain for example a larger set of IoT capability specifications as the result of searches using the weakening of the constraint. In this way the present embodiments relate to the qualities of the information IoT things produce and exchange.

In one illustrative embodiment according to another approach, the present embodiments provide a method for searching IoT systems that retrieves one or more IoT search rules and substitutes constant values for the search parameters of the IoT search rules. The results of these substitutions are referred to as instances of IoT search rules. A search performed using the resulting instances of search rules returns IoT system identifiers and characteristic information of those IoT systems whose characteristic information, when substituted for the IoT system information variables of the search rule instances make all the relations of the search rule instances, true. For IoT information whose data type is numerical, these relations include equality and inequality. For IoT information whose data type is one or more sets together with one or more relations between elements of those sets, referred to here as a relational structure, these relations include equality. More generally, the constraints that occur in the specifications of an IoT search rule may include the relations of a relational structure. In use, for example, this approach may be used to determine a computer-readable language and a set of expressions in this language for the specification of a search rule that represents the specification of an IoT capability.

In one implementation of the present embodiments according to another approach, search results may be retrieved and analyzed to determine which IoT information meet requirements such as, but not restricted to, location of the IoT system on a network, a LAN, WAN or the Internet, or the data type of IoT information. The data type of IoT information is a relational structure, including sets and relations on those sets and operations on those sets. In one implementation of the present embodiments according to another approach the data type of IoT information may be the set of elements of the data type and the set of operations that can be applied to elements of the data type and a set of rules for computing the value of an expression involving applications of operations to the elements of the data type and where the value of an expression refers to the element of the data type of the IoT information that is obtained by the rules for computing of the data type of IoT information and the rules for computing the value are instructions for rewriting an expression containing the operations of the data type of the IoT information. In one implementation of the present embodiments, a report may be generated based on results of applying an IoT search rule and analyzing the search results. In use, for example, this approach may be used to acquire a set of IoT system identifiers for systems that meet an IoT system specification.

In addition to the above, illustrative embodiments of the present embodiments may provide a computer program output in the form of a computer useable medium having a computer readable program. The computer readable program, when executed on a computing device, causes the computing device to perform the method previously described above in conjunction with various devices.

Moreover, illustrative embodiments further provide systems for assessing and improving the performance of the search method of the present embodiments relative to search criteria. In an illustrative embodiment of the system has one or more processors, memory coupled to the processors, and storage devices coupled to the processors. The memory of the system may contain executable instructions which, when executed by the processors, cause the processors to perform the method previously described above.

A method for an IoT system and device, having the steps of: exchanging information with one or more IoT objects; creating domain-specific computer-readable languages to express constraints on the attributes of an IoT information; creating domain-specific computer-readable languages to express constraints on computer-readable names for the attributes of an IoT information, such as temperature, air quality, humidity and the like, in the domains such as energy, automated transportation, building and facility management, supply chain, healthcare and the like; creating domain-specific computer-readable languages to express constraints on computer-readable names for the attributes of IoT information such as upper and lower bounds on temperature values and the like; creating domain-specific computer-readable languages to express constraints on computer-readable names for the attributes of IoT information; creating the composition of constraints on IoT information also known as a specification of IoT information; creating the composition of one or more specifications of IoT information; creating the composition of one or more specifications of IoT information for the purpose or objective of searching over IoT specifications, also known as search rules; creating the composition of two or more specifications of IoT information for the purpose or objective of obtaining a specification of IoT information that results from the compositions of IoT information, also known as IoT information composition; creating IoT specifications in a domain-specific language for purposes of comparing IoT information; creating IoT specifications in a domain-specific language for purposes of comparing the IoT information of two or more IoT by means of comparing their respective IoT specifications by means of the logical relation between the constraints of said IoT specification and the like; wherein two or more IoT specifications may be compared, and wherein the comparison is determined to be equivalent, incomparable or one IoT specification may logically implied by a second IoT specification, performing additional steps including: determining the outcome of a comparison of IoT specification is implicitly and explicitly associated with the one or more pending actions, including determination of differences in the values of CI of the specifications; employing the one or more ML models to generate the one or more risk assessment values that relate to the comparison of IoT specifications or to prediction of the evolution of IoT data over a time interval using machine learning and displaying to a user the results of the comparison, including the one or more comparison outcomes, and one or more predicted risk assessment values that relate to the comparison of IoT specifications or to the predicted evolution of IoT data over a time interval using machine learning; and employing in one implementation relating to healthcare a global positioning systems (GPS) device to provide geo-location information of personal communication devices in order to assess compliance with social distancing requirements or determine one or more risk values for a display to the user, including clustering of persons within a given distance of a designated person and predicting the risk factors associated transmission associated with the movement of infected persons; wherein the geolocation information is employed to select one or more spaces of an enclosed structure for inclusion in one or more of a document, user interface, or report that is used to update a display of these one or more generated risk factors to the user.

A method for an IoT system and device, comprising: exchanging information with one or more IoT objects; producing through the information exchanges information that meets a predetermined objective or purpose; creating descriptions of IoT systems to develop and innovate new accessible IoT systems; providing a means of searching over these descriptions for those satisfying search criteria; and composing two or more specifications, satisfying search criteria, to form a specification of the composition of IoT systems.

An IoT system and device, comprising: one or more IoT objects that exchange information with one another; through the information exchanges, produces information that meets a predetermined objective or purpose; and creates descriptions of IoT systems; provides a means of searching over these descriptions for those satisfying search criteria; and a means of composing two or more descriptions, satisfying search criteria, to form a description of the composition of IoT systems.

These and other features and advantages of the present embodiments will be described or will become apparent to those of ordinary skill in the art, in the following detailed description of the exemplary embodiments in conjunction with the accompanying figures.

BRIEF DESCRIPTION OF THE DRAWINGS

The present embodiments, as well as a non-limiting exemplary mode of use, further objectives and advantages thereof, will best be understood by reference to the following detailed description of an illustrative embodiment when read in conjunction with the accompanying drawings, wherein:

FIG. 4 is a flowchart outlining an exemplary operation of an illustrative embodiment of the present embodiments for registering users, that is, creating a user ID and user IoT List, and adding IoT search results to user IoT List, searching registered IoT, acquiring and processing search results, composing IoT information produced by search results, registering the composed data as an IoT in various combinations and sequences and the like;

Figure 1:
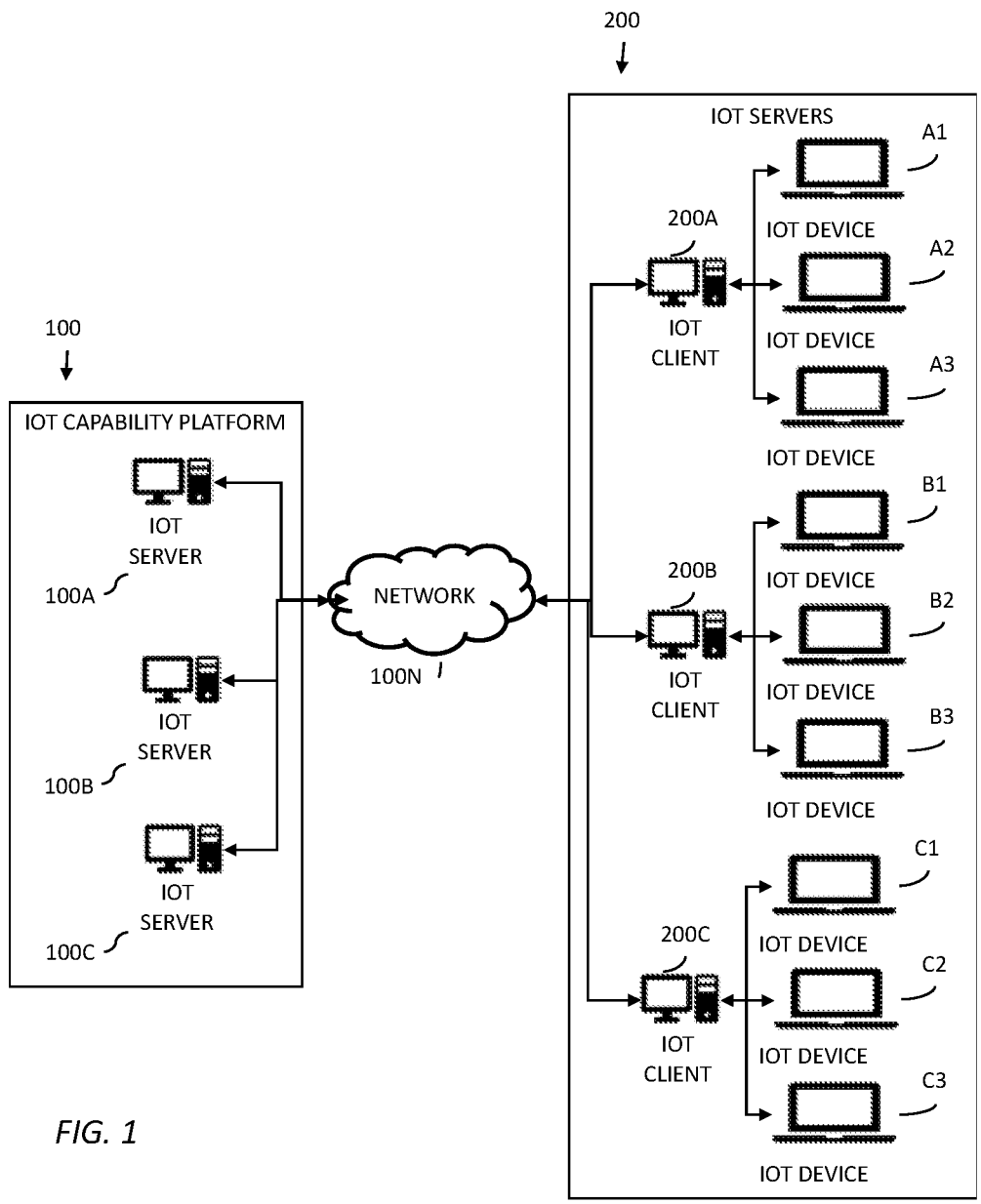
FIG. 1 is an exemplary block diagram of a distributed data processing platform in which aspects of the illustrative embodiments may be implemented.

While the features described herein may be susceptible to various modifications and alternative forms, specific embodiments thereof are shown by way of example in the drawings and are herein described in detail. It should be understood, however, that the drawings and detailed description thereto are not intended to be limiting to the particular form disclosed, but on the contrary, the intention is to cover all modifications, equivalents, and alternatives falling within the spirit and scope of the subject matter as defined herein.

DETAILED DESCRIPTION

The present embodiments relate generally to systems and devices to enable search and composition of Internet of Things information and information and communication technology adapted for the Internet of Things and, more specifically to inter-networking of physical objects ("things") that embed technology enabling the things to sense and collect information from their internal state or their external environment, wherein the information is processed by the things or by other devices, e.g. servers, to be output to the things, to other things or to other devices, and enabling these things to be connected to the Internet either directly or indirectly.

The Internet of Things ("IoT") refers to physical objects which may have embedded technologies such as such as networked sensors and actuators, processing ability, software, combinations thereof and the like, which are able to connect and exchange information over the Internet. An IoT system refers to one or more IoT objects that exchange information with one another and, through those exchanges, produces information that meets a predetermined objective or purpose. An IoT system that refers to a single IoT object may also be referred to as an IoT device. The capability of an IoT system refers to the information produced by the system to achieve its objective or purpose.

The present embodiments may utilize computer software that can be run on a general purpose, networked digital computer or on a dedicated microprocessor as a stand-alone device connected to a digital network. These present embodiments provide a novel means of describing the capabilities of Internet of Things (IoT) systems, using characteristic information of an IoT system, provide a means of reasoning about the composability of IoT systems in terms of this characteristic information and provide a means of composing IoT systems using characteristic information for purposes of innovation.

A useful utility of the present embodiments includes its ability to characterize, log and analyze the information provided by and exchanged between IoT systems as evidence of compliance to policies, such as security policies, and for quality control purposes, such as precision and/or accuracy. Characterization of IoT systems is achieved in the present embodiments by associating with an IoT system attributes of the data of a system and representing those attributes as an ordered set. Analysis of IoT systems is achieved by comparing the values of these attributes, for one or more IoT systems, using a recursive procedure that proceeds along said ordered sets, identifying differences in these attribute values or confirming equality between the same attribute of multiple IoT systems.

Characterization of IoT systems information may be achieved in the present embodiments by associating with data produced by said system attributes of said data and representing said data as attribute values and utilizing constraints on said attribute values expressed in a domain-specific language such as the language of building and facility environment management. Comparison of IoT system information is achieved by comparing the values of these attributes, for one or more IoT systems, using a recursive procedure that proceeds along said ordered sets, identifying differences in these attribute values or confirming equality between the same attribute of multiple IoT systems. This recursive procedure, for example, enables the present embodiments to determine whether two or more IoT systems are the same with respect to values of key attributes of their data.

By analogy, characterization of IoT systems can be achieved in the present embodiments by associating with an IoT system attributes of the data of said system and representing said attributes as a downward growing tree. Analysis of IoT systems can be achieved by comparing the values of these attributes, for one or more IoT systems, using a recursive procedure that proceeds along said tree, identifying differences in these attribute values or confirming equality between the same attribute of multiple IoT systems. This recursive procedure, for example, can enable the present embodiments to determine whether two or more IoT systems are the same with respect to values of key attributes of their data.

As used herein, the terms "machine learning" or "ML", "machine learning module" or "ML module" refer to machine learning models or modules that may be arranged for scoring or evaluating model objects (e.g., documents). The particular type of ML model and the questions it is designed to answer may depend on the application the ML model targets including a user providing or inputting further information. ML models may include models arranged to use different training techniques or statistical techniques, including, linear regression, lasso regression, ridge regression, decision tree, random forest, logistic regression, or the like, or combination thereof. Further, in some embodiments, various heuristic methods or processes may be associated with a ML model including a user providing or inputting further information. In some embodiments, configuration information may be employed to configure or select one or more ML model for a particular embodiment or application, or the like, or combination thereof.

Critical applications of the present embodiments may include supply chain resilience, performance and security of mobile IoT systems such as transportation systems, identification and mitigation of cyber-physical threats to infrastructure and monetizing IoT information.

For example, supply chains, in the public and private sectors, are subject to disruption and failure during surges in demand for goods and services or reduction in availability of goods and services. IoT systems are widely deployed across supply chains in all of their components, including materials, manufacturing, ordering and distribution, shipping and logistics, marketing, contracts and payment. The present embodiments can be applied to this IoT information to build and statically check the feasibility of current supply chains and propose alternative supply chains during disruption. The system in one embodiment generates a report to the user computing device relating to failures of one or more of the components of a supply chain, such as shipping or logistics components, and using temperature IoT or GPS position IoT may propose a solution, such as modifying or replacing the shipping or logistics component of the supply chain and implement the solution if configured to do so by a user. The system in one embodiment may accept further inputs from the user based on the report to the user and may using a machine learning model or module be so trained to recognize and classify instances failures of supply chain components and propose and implement a solution, such as to modify the IoT or IoT data. Additionally, the system in one embodiment may accept further inputs from the user based on the report to the user and may use a machine learning model or module be so trained to recognize and classify supply chain IoT data, including data including temperature and GPS position over a time interval, to predict potential failures of supply chain components and propose and implement a solution, such as to modify the IoT or IoT data in order to prevent potential failures.

Mobile IoT systems are deployed in manufacturing automation and robotics and communication and transportation systems. Awareness of their current capabilities and status, including location and operational status, is critical to their efficiency and effectiveness. The present embodiments can be applied to provision, maintain and assess the trustworthiness of such IoT systems through its composability checks on IoT information and monitoring of its compliance to policies. Policies related to protective measures in a health emergency caused by the spread of communicable disease, such as social distancing, is such an application using global positioning functions of personal communication devices. In one implementation of the present embodiments a personal communication device is regarded as IoT capability that indicates using a global positioning system (GPS) or device the current location of its owner. A data quality policy requiring compliance to social distancing rules is implement by the system by acquiring positioning data from such devices within a space of designated size by calculating the distance between the acquired positioning data. This system with a GPS device may also calculate the size of a group or cluster of people within a certain radius of a predetermined user and may also assess the risk of transmission of infectious disease and improve estimates of risk using a machine learning module trained using actual changes in infection rates based on positioning data and position data trends for personal communication devices of infected persons.

The physical systems monitored and controlled by IoT systems are vulnerable to attacks composed to their cyber, physical and human components. By enabling access and composition of information from these systems, the present embodiments broaden the cybersecurity perspective to include IoT systems embedded in mechanical functions and human, or operator, functions. The present embodiments can merge and compose information from all three components and offers a means of creating, managing and assuring cyber-physical security services, such as physical governance of cyber activity in deployments.

The information produced by individual IoT systems may be of business value to the owner but may also be of value to other private or public entities, in its current form or modified through computation or in combination with the information taken from a multiplicity of sources or other IoT systems and modified for a new or better use, including through simple modification such as conversion of units or through a machine leaning module trained by a user. Once a business value is identified, as is or in combination with other IoT systems' information, the present embodiments assists in identifying the sources of such information, composing them if necessary and forming the characteristic information needed to form and market the IoT information whose business value has been identified. In so doing, these embodiments provide a means of monetizing IoT information.

Figure 2:
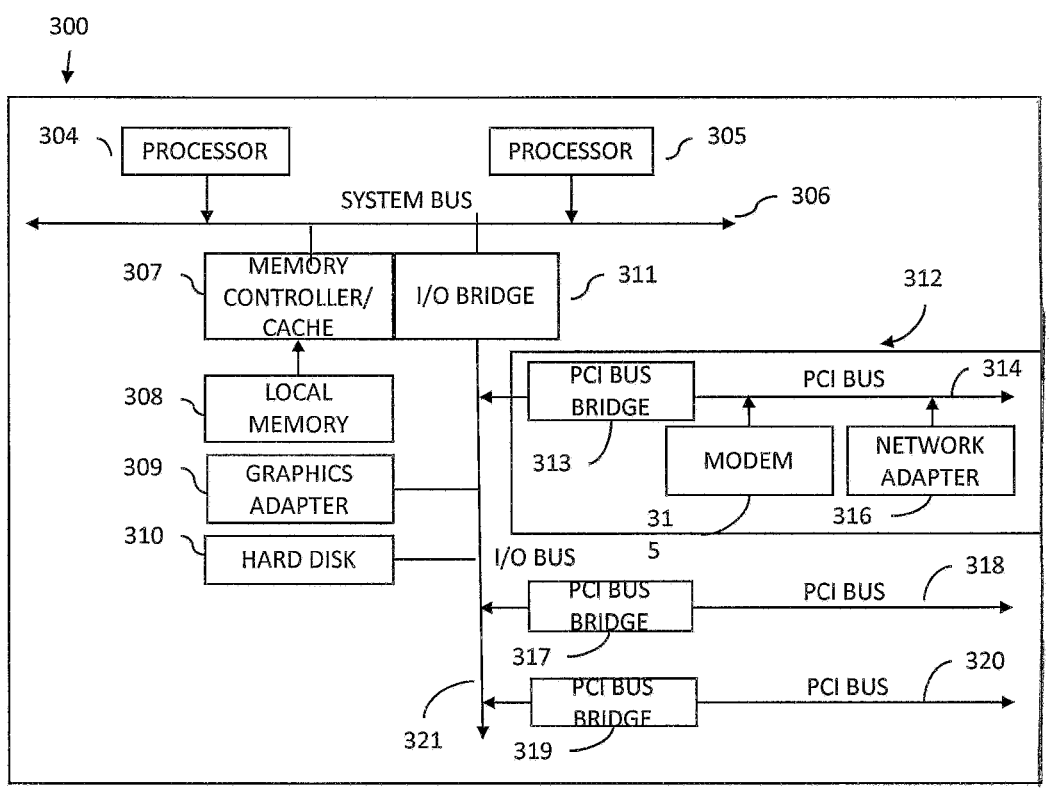
FIG. 2 is an exemplary block diagram of a computing device in which aspects of the illustrative embodiments may be implemented.

Illustrative embodiments of the present embodiments provide mechanisms for registering, searching and monitoring the compliance of IoT system information to criteria set forth in an IoT information quality policy. As such, the mechanisms of the illustrative embodiments are especially well suited for implementation in a distributed data processing system having a plurality of computing devices that communicate with one another by way of one or more networks. FIGS. 1-2 are provided as examples of a distributed data processing system, server computing device, and client IoT in which exemplary aspects of the illustrative embodiments of the present embodiments may be implemented. It should be noted that the example computing environments illustrated in FIGS. 1-2 are not intended to state or imply any limitation as to the particular types of computing environments in which the exemplary aspects of the illustrative embodiments of the present embodiments may be implemented. Rather, many modifications to the depicted computing environments may be made without departing from the spirit and scope of the present embodiments.

With reference now to the figures, FIG. 1 IoT Capability Platform is a pictorial representation of a network of data processing systems in which the present embodiments may be implemented. Network data processing system 100 is a set of networked computers 100A-100C in which the present embodiments may be implemented. Network data processing system 100 connects to a network 100N, which is the medium used to provide communications links between an instance of the present embodiments 100 and various IoT and computer servers 200, comprising IoT Client computing devices 200A, 200B, and 200C, connected together by a network connected to network 100N and each connected to a network of IoT devices. Network 100N may include physical connections, such as wire, wireless communication links, or fiber optic cables and may be an intranet, wide area network or the Internet.

In the depicted example, the IoT servers 100A-100C are connected to network 100N and IoT Clients 200A, 200B, and 200C are connected to network 100N. These IoT Clients 200A, 200B, and 200C may be, for example, networked IoT devices or networked computers that collect and process and send processed data, acquired from networked IoT devices to the network of IoT Clients 200A, 200B, and 200C. In the depicted example, IoT server 200A sends requests and acquires data from IoT devices A1-A3; IoT server 200B sends requests and acquires data from IoT devices B1-B3; and IoT server 200C sends requests and acquires data from IoT devices C1-C3. IoT Clients 200A, 200B, 200C are clients to their respective sets of IoT devices A1-A3, B1-B3 and C1-C3, respectively and IoT devices A1-A3, B1-B3 and C1-C3 are servers to IoT Clients 200A-200C.

Network data processing system 100 may include additional servers, clients, and other devices not shown. In the depicted example, the network of the network data processing system is the Internet network 100N representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, having thousands of commercial, government, educational and other computer systems that route data and messages. Network data processing system 100 also may be implemented as a number, one or more, of different types of networks, such as for example, an intranet, a local area network (LAN), or a wide area network (WAN). FIG. 1 is intended as an example, and not as an architectural limitation for the present embodiments.

Referring to FIG. 2, a block diagram of a data processing system that may be implemented as an IoT server such as IoT Servers 100A-100C or as IoT Clients 200A-200C or as IoT Devices A1-A3, B1-B3 and C1-C3 in FIG. 1, depicted in accordance with an illustrative embodiment of the present embodiments. Data processing system 300, referring to FIG. 2, may be a symmetric multiprocessor (SMP) system including a plurality of processors 304 and 305 connected to system bus 306. Alternatively, a single processor system may be employed. Also connected to system bus 306 is memory controller/cache 307, which provides an interface to local memory 308. I/O Bus Bridge 311 is connected to system bus 306 and provides an interface to I/O bus 321. Memory controller/cache 307 and I/O Bus Bridge 311 may be integrated as depicted.

Peripheral component interconnect (PCI) bus bridge 313 connected to I/O bus 321 provides an interface to PCI local bus 314. A number of modems may be connected to PCI local bus 314. Typical PCI bus implementations will support multiple PCI expansion slots or add-in connectors. Communications links to IoT devices 200A1-200a3 in FIG. 1 may be provided through modem 315 and network adapter 316 connected to PCI local bus 314 through add-in connectors.

Additional PCI bus bridges 317 and 319 provide interfaces for additional PCI local buses 318 and 320, from which additional modems or network adapters may be supported. In this manner, data processing system 300 allows connections to multiple network computers. A memory-mapped graphics adapter 309 and hard disk 310 may also be connected to I/O bus 321 as depicted, either directly or indirectly.

Those of ordinary skill in the art will appreciate that the hardware depicted in FIG. 2 may vary. For example, other peripheral devices, such as optical disk drives and the like, also may be used in addition to or in place of the hardware depicted. The depicted example is not meant to imply architectural limitations with respect to the present embodiments.

The data processing system depicted in FIG. 2 may be, for example, a server system, running the Windows operating system, Apple OS operating system, Advanced Interactive Executive (AIX) operating system, LINUX operating system, or the like.

As shown, an operating system runs on processor 304 and is used to coordinate and provide control of various components within data processing system 300 in FIG. 2. The operating system may be a commercially available operating system, such as sold under the name WINDOWS, which is available from Microsoft Corporation. An object-oriented programming system such as Java may run in conjunction with the operating system and provide calls to the operating system from Java programs or applications executing on data processing system 300. "Java" is a trademark of Sun Microsystems, Inc. Instructions for the operating system, the object-oriented programming system, and applications or programs, including those of the present embodiments, are located on storage devices, such as hard disk drive 310, and may be loaded into main memory 308 for execution by processor 304.

Those of ordinary skill in the art will appreciate that the hardware in FIG. 2 may vary depending on the implementation. Other internal hardware or peripheral devices, such as flash read-only memory (ROM), equivalent nonvolatile memory, or optical disk drives and the like, may be used in addition to or in place of the hardware depicted in FIG. 2. Also, the processes of the present embodiments may be applied to a multiprocessor data processing system.

As a further example, data processing system 300 may be a personal digital assistant (PDA) device or a smartphone, which is configured with ROM and/or flash ROM in order to provide non-volatile memory for storing operating system files and/or user-generated data.

Figure 3:
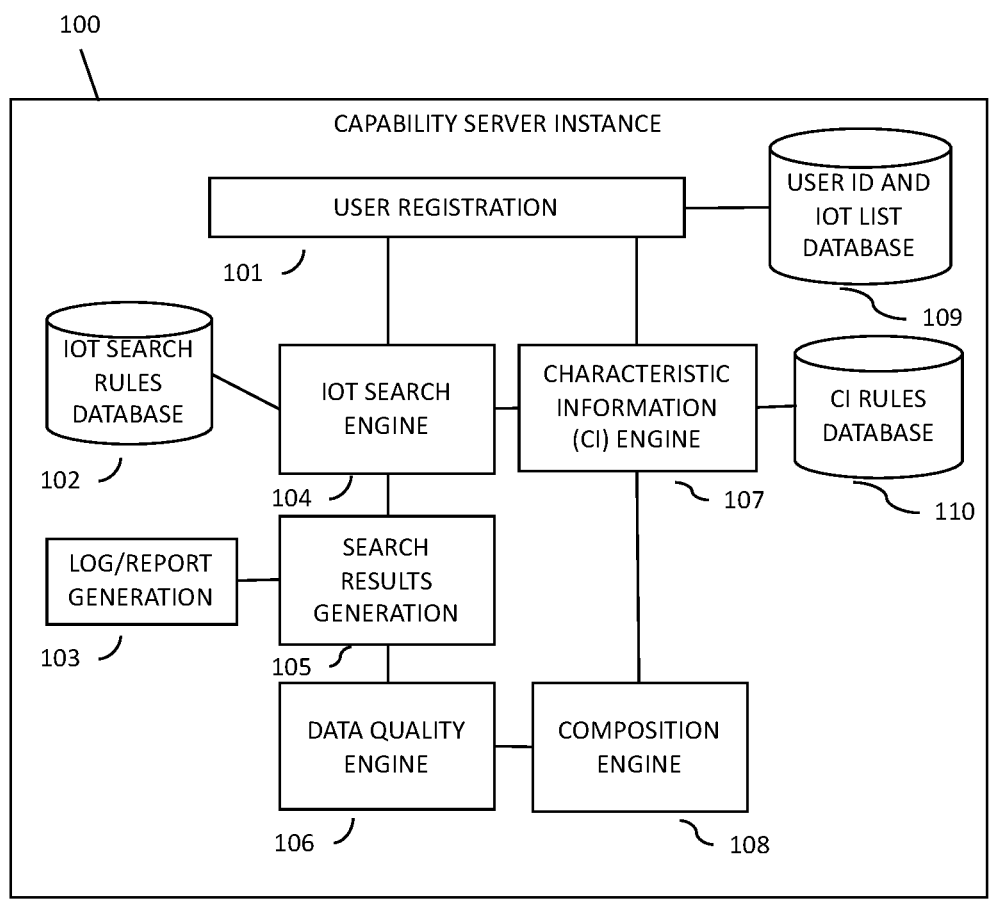
FIG. 3 is an exemplary diagram illustrating operational elements of an illustrative embodiment.

The depicted example in FIG. 3 and above-described example are not meant to imply architectural limitations. For example, data processing system 300 also may be a notebook computer or hand-held computer in addition to taking the form of a PDA or a smartphone. Data processing system 300 also may be a kiosk or a Web appliance.

With reference again to FIG. 1, the illustrative embodiments include an IoT search engine that may be resident on IoT Clients 200A-200C and/or may be downloaded to IoT devices A1-A3 and B1-B3 and C1-C3 from clients such as IoT Clients 200A-200C. The IoT search engine is provided for searching one or more IoT Clients 200A-200C for IoT systems and IoT system information that meet search criteria.

The present embodiments may identify an IoT or IoT system by a unique ID and a set of characteristic information (CI) of the IoT or IoT system. The CI of an IoT or IoT system comprises, for example, the data units or data types of IoT data produced by the IoT or IoT system, for example, temperature, geolocation or URL or the like, or combinations thereof. The search criteria of the IoT search engine of the present embodiments are sets of IoT search rules. The IoT search rules of the present embodiments comprise relations between different sorts of variables, including constraint variables and IoT CI variables. An instance of an IoT search rule may be obtained from an IoT search rule by substituting constant values, determined by the User performing the search, for the constraint variables of the IoT search rule. Performing the IoT search, based on instances of an IoT search rules, may return as value of the search the list of IoT IDs and their respective CI that satisfy the instance of the IoT search rule. An IoT ID and CI satisfy an instance of an IoT search rule if, substituting the CI of the IoT for the IoT variables of the instance of the search rule makes all the relations of the instance of the search rule true. For IoT data whose unit type or data type is numerical, these relations include equality and inequality. More generally, the relations of an IoT search rule may include the relations of an algebraic structure.

The IoT search rules may be maintained, stored and managed, on IOT servers 100A-100C or in a separate storage system.

The CI of IoT or IoT systems, and so also IoT search rules, may further include rules for searching for indicators of IoT data quality, including refresh rate or in meta-information associated with the IoT and the like. The IoT search rules, of embodiments of the present embodiments, may also comprise IoT search rules for patterns of CI that identify IoT data that contains specific information, such as confidential or personally identifiable information (PII). The IoT search rules in a specific embodiment of the present embodiments may include rules identifying various types of IoT or IoT systems, including sets of IoT search rules for identifying IoT or IoT systems that possess specific computer program application types, formats, and the like.

The IoT search engine, on IoT servers 100A-100C for example, may remotely administer searches of IoT Clients 200A-200C. The IoT search engine may make use of an IoT Client computing device, which may be stored on the server or another storage system to retrieve information about IoT Clients 200A-200C that are to be searched using the mechanisms of the IoT search engine.

In remotely administering searches of IoT Clients 200A-200C, the IoT search engine may download or transfer a client agent to the IoT Clients 200A-200C which runs the client agent to collect information from the IoT Clients 200A-200C and provides the results of the search back to IoT servers 100A-100C. For example, the client agent may collect information about the IoT present on the IoT client computing device and provide this information back to the servers for analysis using the IoT search rules. Alternatively, the client agent may actually perform the search of IoT devices on the client IoT Clients 200A-200C using the IoT search rules present on the IoT servers 100A-100C. In remotely administered searches where the client agent collects information about the IoT present on the IoT client computing device and provides this information back to servers for analysis using the IoT search rules and the analysis shows for example that the information about the IoT present on the IoT client computing device do not satisfy the criteria of the search rule, the system generates a report to the user computing device and may propose a solution, such as modifying the client agent, and implement the solution if configured to do so by a user.

For IoT and IoT data meeting one or more criteria set forth in IoT search rules, characteristic information may be gathered about these IoT or IoT systems. This characteristic information may include, for example, the ID of the IoT or IoT system, the criteria met by the IoT or IoT data, the CI of the IoT data, information identifying the data quality protection mechanisms currently applied to the IoT on the client IoT, and the like. This characteristic information may be used by the IoT search engine to determine if the IoT is being maintained in accordance with one or more criteria set forth in the IoT search rules and in case the IoT is not being maintained in accordance with one or more criteria in the IoT search rules the system generates a report, informs a user, and may using a machine learning model or module be so trained to recognize and classify instances maintenance failures and propose and implement a solution, such as to modify the IoT or IoT data.

The IoT search engine may use the characteristic information gathered about IoT and IoT data to identify one or more data quality policies in an IoT search rules database, which may also be stored on the IoT servers 100A-100C or a separate storage system, that apply to those IoT or IoT data. The IoT data quality policies may then be applied to the characteristic information gathered about an IoT or IoT data to determine if the IoT or IoT data is being maintained in compliance with applicable data quality policies. Results of the application of data quality policies may be logged and maintained in an IoT Client database, for example. In addition, the results may be used to generate reports and notifications that are sent to the IoT Clients 100A-100C and/or an administrator's computing device. In this way, the user of the IoT Clients 100A-100C and/or the administrator may be notified of any violations of the data quality policy by IoT or IoT data maintained on the IoT Clients 100A-100C. Moreover, solutions for placing an IoT or IoT data in compliance with the data quality policy may be provided by the system as part of the log, report and/or notification and be implemented by the system if so enabled by the user.

In a further embodiment, the IoT search engine may be distributed from IoT servers 100A-100C to the IoT Clients 200A-200C, referred to here as IoT Client-based search engine, such that the IoT search engine is run on the IoT Clients 200A-200C and results are provided back to the IoT servers 100A-100C for logging and reporting. In such an embodiment, IoT search rules in the IoT Search Rules Database 102 of FIG. 3 may be provided to the IoT Clients 200A-200C such that these rules are applied by the IoT search engine in searching the IoT Clients 200A-200C on which the IoT search engine runs. Because these IoT search rules may be updated from time to time, the IoT Client-based IoT search engine may periodically communicate with the IoT servers 100A-100C to download the most recent updates to the IoT search rules to the IoT Client computing devices 200A-200C and a machine learning module of the system may update the IoT search rules based on user inputs in response to the performance of these search rules.

Results of IoT search of the IoT Clients 200A-200C may be returned to the IoT servers 100A-100C which may then apply the data quality policies to these search results as discussed previously. Alternatively, in a similar manner as the IoT search rules, the data quality policies may be downloaded to the IoT Clients 200A-200C such that the application of the data quality policies to the results of IoT search may be performed on the IoT Clients 200A-200C.

Results of the application of the data quality policies to the results of IoT search may be logged and maintained in the IoT servers 100A-100C and/or in the IoT Clients 200A-200C and may be reported to the user of the IoT Clients 200A-200C and/or an administrator in a similar manner as previously discussed.

The IoT search engine may be run on the IoT Clients 200A-200C in accordance with a schedule established by a user of the IoT Clients 200A-200C. The schedule is preferably established such that the IoT search is performed and the data quality policy is applied, referred to here as a data quality search, at a time when such a data quality search will not interfere with normal operation of the IoT Clients 200A-200C by a user. Alternatively, the IoT search engine may include a module for monitoring the current activity of the IoT Clients 200A-200C and may initiate the data quality search at a time of detected inactivity of the IoT Clients 200A-200C. For example, if the IoT Clients 200A-200C enter a sleep state, for example, such as when a screensaver is initiated, or the user logs-out of the IoT client 200A-200C but leaves the IoT client 200A-200C running, the IoT search engine may initiate a IoT search of the IoT client 200A-200C.

In addition, in order to ensure that the IoT search engine is run periodically on the IoT client 200A-200C, the IoT server 100A-100C may maintain information in the IoT client database identifying a last time that the IoT search engine was run on each IoT client 200A-200C. The IoT server 100A-100C may remotely initiate the running of the IoT search engine on the IoT client 200A-200C when the elapsed time from the last time the IoT search engine was run on that IoT client 200A-200C exceeds a predetermined threshold.

As mentioned above, the IoT search engine makes use of IoT search rules that determine the manner by which the IoT search engine identifies IoT or IoT data of interest to the user, for example, confidential information that may be a violation of a data quality policy implementing security. These IoT data may be, for example, electronic documents, electronic images, electronic files, compilations of data, objects in an object-oriented environment, or other units of data. IoT search rules may be established for various types of IoT data, for example, various file formats such as Microsoft Word™ documents, Adobe Acrobat™ documents, JPEG image files, bitmap image files, Freelance Graphics™ files, Microsoft PowerPoint™ files, Microsoft Excel™ files, and the like. IoT search rules may be established for identifying particular filename patterns indicative of, for example, confidential information being contained in the files, e.g., a filename with the string "secret," "confidential," "_c," "_s," or the like.

The IoT search rules may further designate text strings to be looked for in the actual IoT data of the IoT or IoT system. Thus, for example, an IoT search rule may include search in the IoT data of an IoT or IoT system to determine if it includes, e.g., "personally identifiable information", or the like, and highlight in its report the violation of a data quality policy prohibiting this information, or the like.

The data quality policy may further dictate, for example, that any IoT or IoT system found to be in violation of the data quality policy must be viewed by the user of the IoT client no later than a specified number of days from a date of the IoT search or that the IoT or IoT data must be viewed by the user by a certain time. User may input further information to train a machine learning module to recognize violations or patterns of use that could lead to a violation. In such a case, such IoT data may be automatically deleted after viewing by the user. As a result, the violation may be logged, and a report sent to the user of the IoT client 200A-200C and/or an administrator or other data quality monitor's computing device. This report may designate the data quality policy that has been violated, the IoT that has been determined to be in violation of the data quality policy, and may provide information as to how the user of the IoT client 200A-200C may bring his IoT client 200A-200C back into compliance with data quality policies with regard to the identified IoT or IoT system. Other information may also be provided in the report in addition to, or in replacement of, the information noted above.

Thus, the illustrative embodiments presented herein provide mechanisms for searching an IoT client for IoT that are in violation of data quality policies and obtaining characteristic information regarding the manner by which the IoT device is being maintained in the IoT client. The illustrative embodiments further provide mechanisms for determining whether the manner by which the IoT or IoT system is being maintained in the client IoT computing device violates any established data quality policies. The illustrative embodiments also provide mechanisms for reporting data quality policy violations and providing information regarding how to bring IoT client back into compliance with the established data quality policies.

Figure 4:
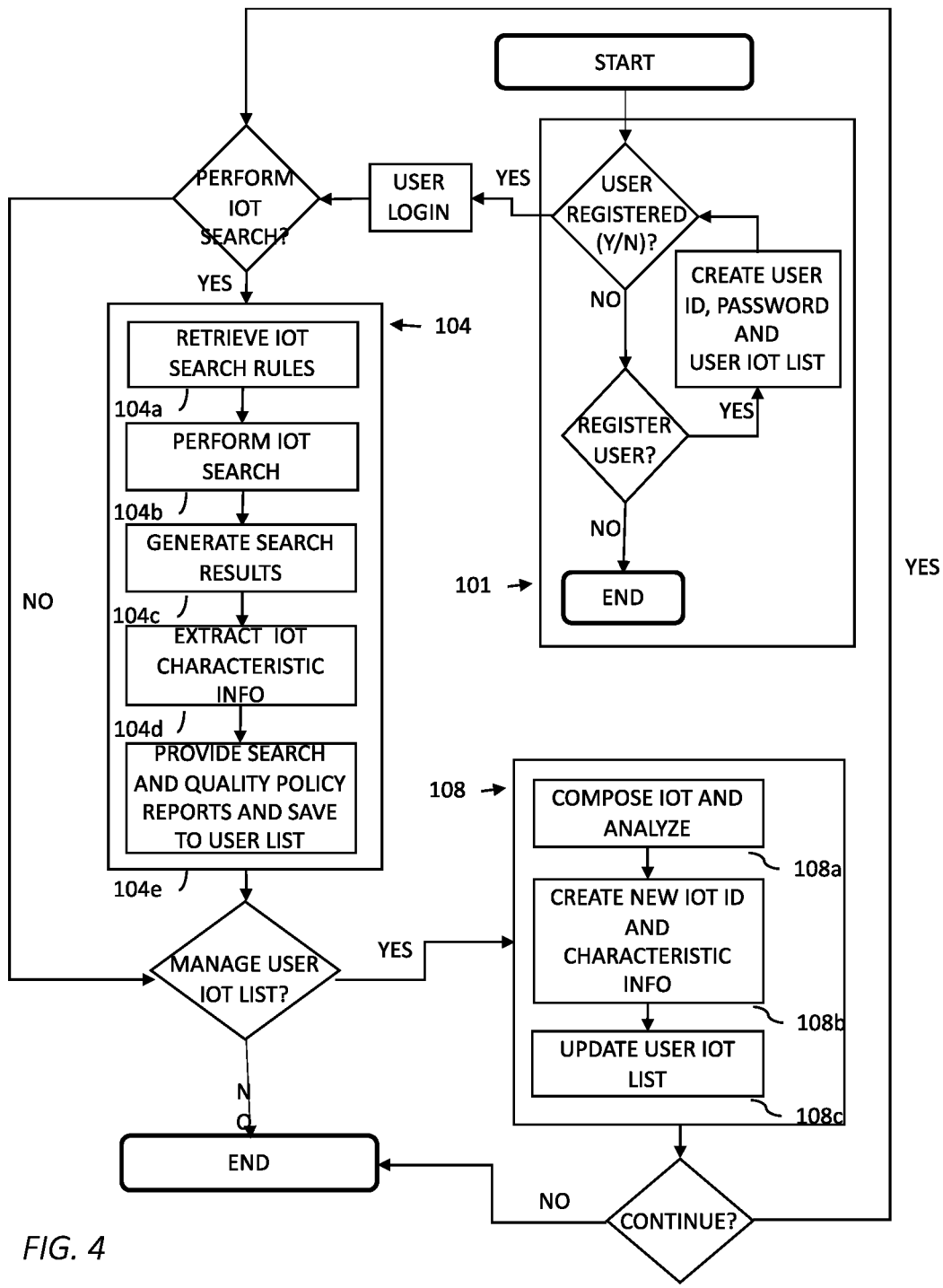

Referring to FIG. 4, a flowchart outlining an exemplary operation of the present embodiments is provided for registering users, performing an IoT search, including creating a user ID and User IoT List, and composing IoT or IoT systems and adding the composed IoT to the User IoT List.

In the illustrative embodiment, as depicted in FIG. 4, a user enters the system of the present embodiments and is able to login or to create login credentials, including username and password. Once logged in, the User is able to perform an IoT search using the IoT search engine 104 or manage the User IoT List 108, including storage of IoT search results and the storage of the result of the User composing IoT.

To perform an IoT search, using the IoT search engine 104 of the illustrative embodiment of the present embodiments, the User retrieves one or more IoT search rules 104a from the IoT search rules database 102. Instances of the retrieved IoT search rules are obtained through the User providing constant values for the constraint variables of the retrieved IoT search rules. The User determines which IoT search rules to retrieve from the IoT search rules database 102 by choosing the characteristic information deemed relevant to the User's search, for example the unit type or data type the IoT data, geolocation of the IoT device or URL, or other network locator, of the IoT device and the like.

To perform an IoT search the User submits instances of IoT search rules 104b to the IoT search engine 104. On submission of an instance of IoT search rules, the IoT search engine 104 performs the IoT search 104b by substituting, for the search variables of the IoT search rule instance, the CI of each IoT currently registered to the system of the present embodiments and generates the set of search results 104c comprising the set of IoT currently registered to the system of the present embodiments wherein the substitution of the CI of said IoT into the instance of the IoT search rule results in a true statement about the CI of said IoT. Following the generation of IoT search results 104c the system of the illustrative present embodiment will extract the CI of each of the search results 104d. The system of the illustrative present embodiment will apply any data quality policies, designated or scheduled by the User, to the CI of each of the search results and create a search and data quality policy reports and save these reports to the User IoT List of the User 104*e*.

After a run of the IoT search engine by the User, the system of the present illustrative embodiment will query the User as to whether the User will manage the User's IoT List.

The User, having opted to manage the User IoT List after performing IoT search or directly after login may operate the composition engine 108 of the present illustrative embodiment by retrieving a set of IoT from the User IoT List and composing 108*a* the data of the set of IoT retrieved from the User IoT List and analyzing the result of composition 108*a* to determine the CI of the data resulting from composition. After performing composition and analysis to obtain the CI of the data resulting from composition the system of the present illustrative embodiment will create an ID, combine the ID with the CI of the composition 108*b* and will update the IoT List of the User 108*c* with the ID and CI of the composed IoT.

The User, having updated the User IoT List 108*c* has the option to continue or END work in the system of the present illustrative embodiment. Should the User choose to continue, the User will once again have the option of either performing an IoT search or managing the User IoT List, comprising adding, updating or deleting ID and CI of IoT in the User IoT List. Should the User choose to END work in the system of the present illustrative embodiment, the User will be logged out of the system.

Figure 5:
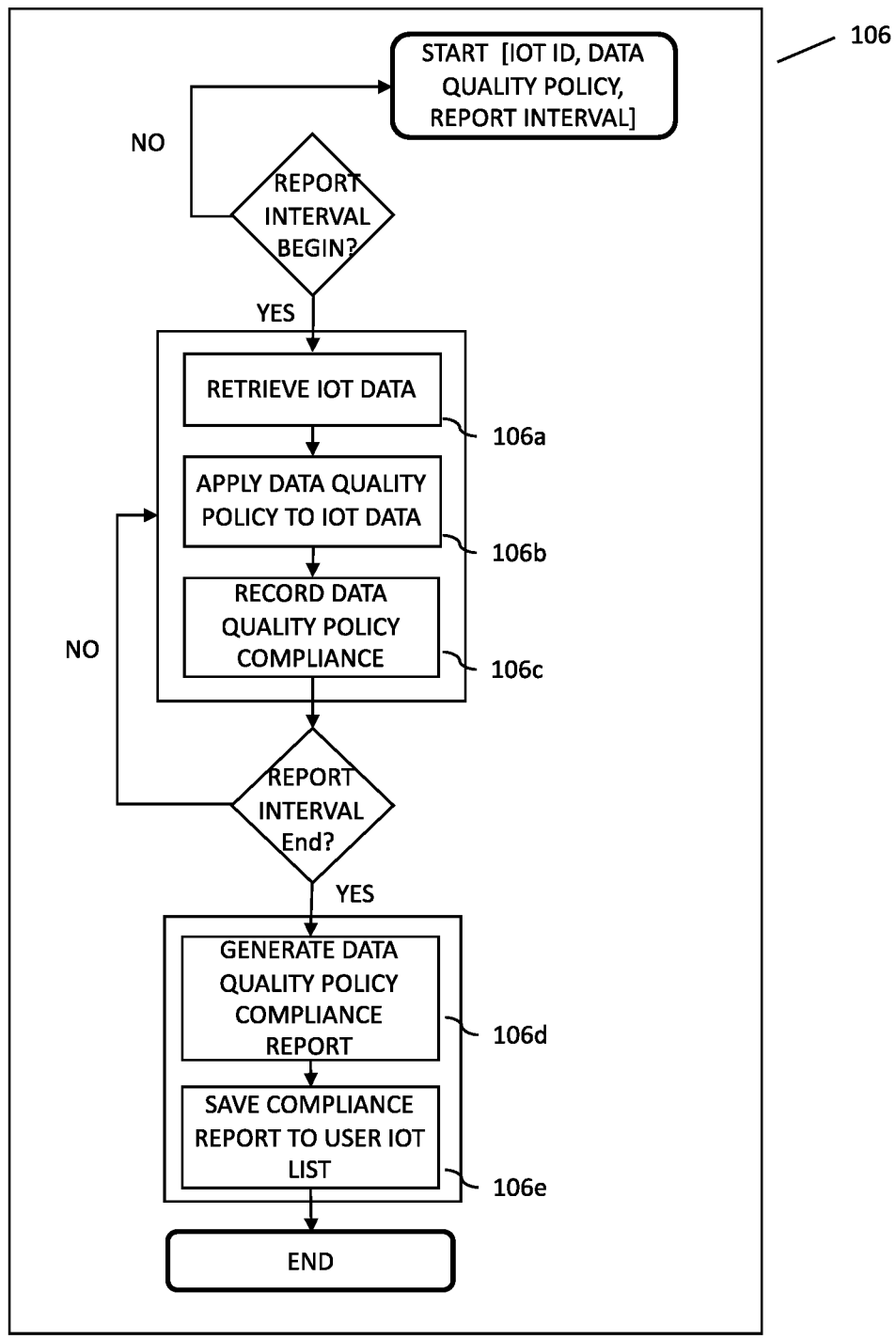
FIG. 5 is a flowchart outlining an exemplary operation of an illustrative embodiment of the present embodiments for manual or automated assessment of the quality IoT information, or in accordance with an information quality policy in the form of constraints on the characteristic information of IoT systems.

Referring to FIG. 5, a flowchart is depicted describing an exemplary operation of the Data Quality Engine 106 of one approach to the present embodiments. A data quality policy in an illustrative embodiment may include a set of instances of IoT search rules whose constraints are applied, manually or in accordance with a scheduled report interval established by the User, to IoT and IoT data and their characteristic information to determine whether the constraints of the data quality policy are satisfied by the IoT and IoT data or not. Referring to FIG. 5, the User may provide to the Data Quality Engine 106 an IoT ID, a data quality policy and a report interval, a start and finish time over which the Data Quality Engine 106 is requested to apply the data quality policy to the IoT and IoT data.

Referring to FIG. 5, in a present illustrative embodiment the application of a data quality policy is initiated at a User determined start time and over a predetermined interval of time. Current IoT data values are retrieved 106*a* for the IoT, whose ID is provided by the User. The data quality policy is applied 106*b* to the current IoT data values of the IoT, whose ID is provided by the User and compliance of the current IoT data values of the IoT is recorded 106*c*. If the report interval end time is achieved in the illustrative embodiment, then a data quality policy compliance report may be generated 106*d* and the data quality policy compliance report is saved to the User IoT List 106*e*. In an illustrative embodiment the application of a data quality policy through the Data Quality Engine 106 may be applied manually at the request of the User or may be applied at a time or times scheduled by a User. Data quality policies are also specifications and include constraints on IoT information, including constraints on IoT information over intervals of time determined by a user. The system provides quality compliance reports to a user, a user inputs further information in response to the report and a Machine Learning Module is trained to recognize and classify patterns of data over intervals of time such as training to learn to review violations or identify patterns of use that could lead to violations.

Figure 6:
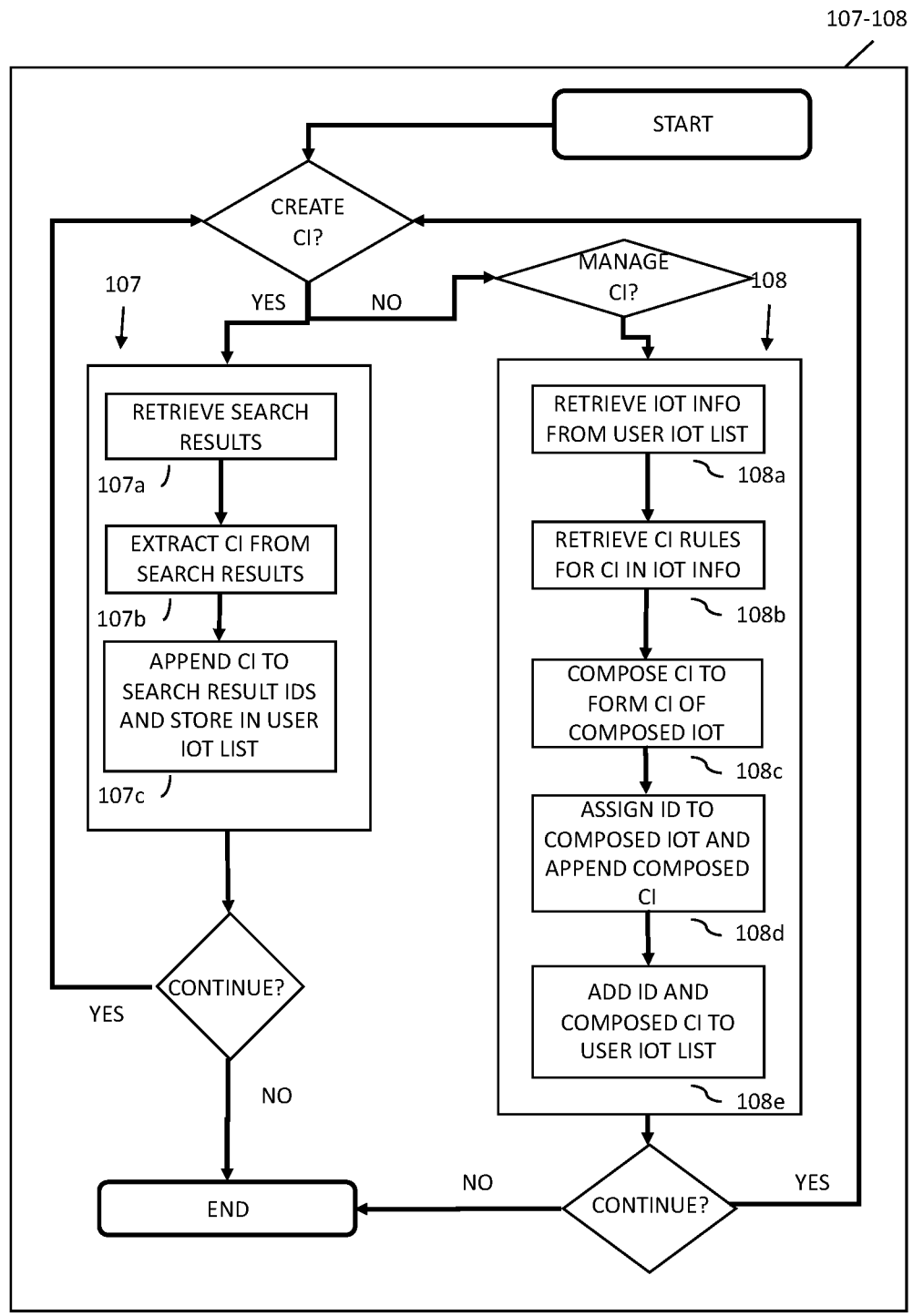
FIG. 6 is a flowchart outlining an exemplary operation of an illustrative embodiment for creating, capturing in electronic form and storing the characteristic information of IoT.

FIG. 6 is a flowchart depicting an exemplary operation of the Characteristic Information Engine 107 and an exemplary operation of the operation of managing characteristic information for IoT or IoT systems composed using the Composition Engine 108, in an illustrative embodiment. The Characteristic Information Engine 107 performs the operations of creating and managing the characteristic information (CI) of IoT or IoT systems.

Referring to FIG. 4, the User of an illustrative present embodiment may register as a User, perform IoT or IoT system searches, compose and analyze IoT or IoT systems, create ID and CI for composed IoT or IoT systems and update the User IoT List. Referring to FIG. 6, the User may create CI 107 or manage CI 108. If the User chooses to create CI 107 an illustrative embodiment of the present embodiments would retrieve search results 107*a*, extract the CI of the search results 107*b*, append the CI to the ID of each search result and store the result in the User IoT List 107*c* wherein the user can input further information related to the search criteria which allows the system to propose a solution, including modification of the constraints of the search criteria, and implement the modification to develop its own search criteria.

If the User chooses not to create CI 107 but to manage CI 108 the User of an illustrative embodiment of the present embodiments would retrieve IoT information from the User IoT List 108*a*, retrieved CI rules for the CI in the IoT information 108*b*, compose CI to form the CI of composed IoT or IoT systems 108*c*, assign an ID to the composed IoT and append the composed CI of 108*c* to the ID 108*d* and add the ID and composed CI to the User IoT List 108*e*.

Referring to FIG. 6, the User may continue to create CI 107 or choose to manage CI 108, or to end the session.

Figure 7:
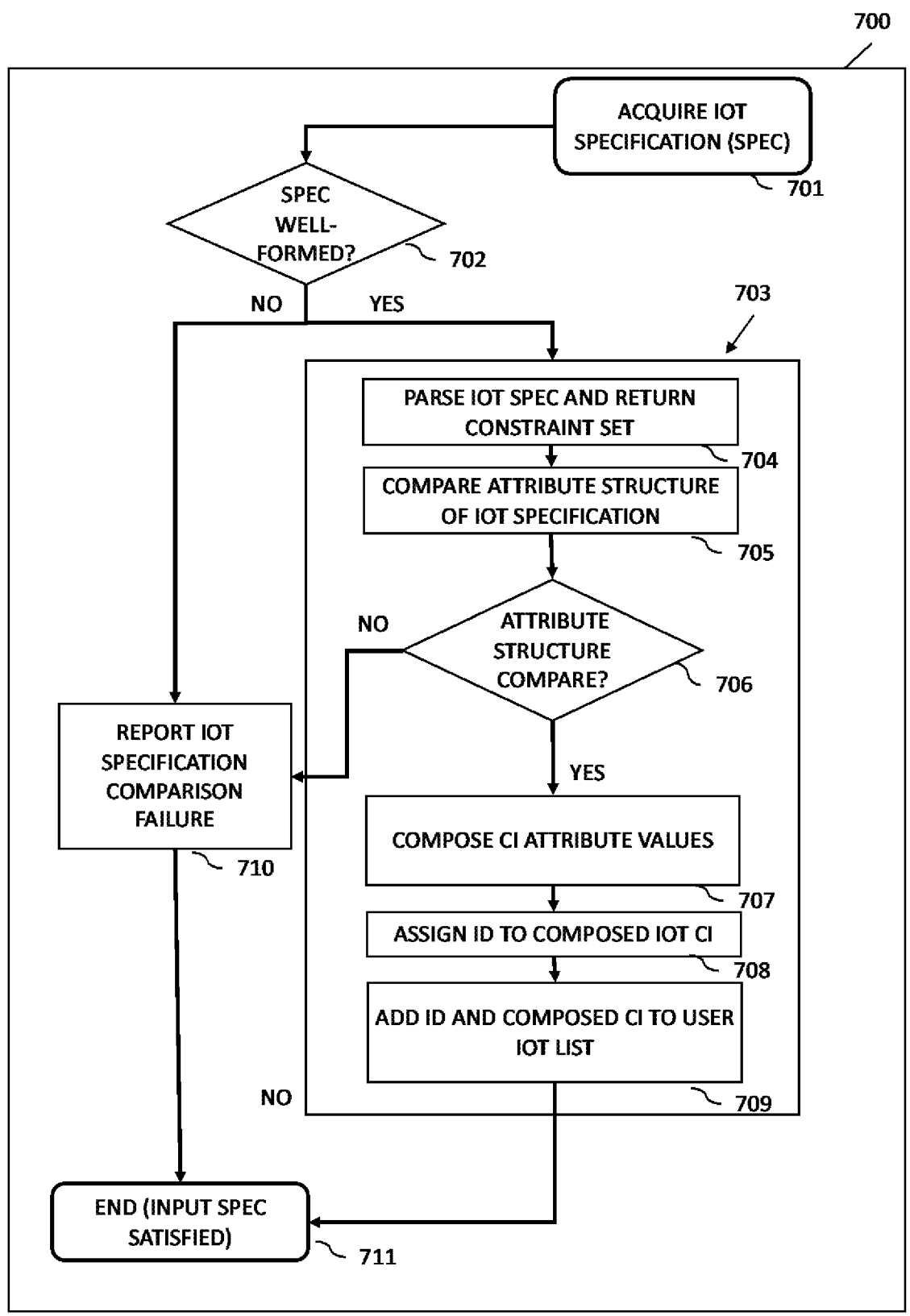
FIG. 7 is a flowchart describing an exemplary operation of a Characteristic Information Engine.

FIG. 7 is a flowchart describing an exemplary operation of the Characteristic Information Engine 107 as it relates to searching for IoT specifications that satisfies the constraints of a given IoT specification, whether for purposes of IoT search or application of an IoT data quality policy, and an exemplary operation of the operation of managing specifications for IoT or IoT systems composed using the Composition Engine 108, in an illustrative embodiment. The Characteristic Information Engine 107 in addition to performing the operations of creating and managing the characteristic information (CI) of IoT or IoT systems also performs the comparison of two IoT specifications that generates a report to a user, a user inputs further information on the basis of the report which allows the system to propose a solution to modify the IoT device or system and to implement a solution.

The flowchart depicted in FIG. 7 describes an exemplary operation of the Characteristic Information Engine 107 as it relates to the comparison of an IoT specification to the search or IoT data quality specification and as it relates to the implementation of the functions of search and of assessing the quality of the IoT information that make up an IoT capability. The Characteristic Information Comparison 700 is initialized with an IoT specification referred to as the initializing IoT specification. Having acquired an IoT specification 701, referred to as the input IoT specification, the Characteristic Information Comparison 700 assesses whether the input specification is well-formed 702 wherein being well-formed corresponds to each of the constraints in the input specification being the application of one or more of the relations of the relational structure of the input specification to the elements of the one or more of the sets in the relational structure of the input specification.

Should any of the constraints of the input specification fail to be the application of one or more of the relations of the relational structure of the input specification to the elements of the one or more of the sets in the relational structure of the input specification, then a report is generated of failure 710. Should all the constraints of the input specification be the application of one or more of the relations of the relational structure of the input specification to the elements of the one or more of the sets in the relational structure of the input specification, then the comparison operation 703 is applied to the input specification.

The comparison operation 703 parses the input specification 704 and returns as its value the set of constraints of the input specification. The comparison operation 703 compares the attribute structure of the input specification to the attribute structure of the initializing specification. Should the attribute structure of the input specification fail to be contained in, or fail to be a subset of, the attribute structure of the initializing specification 706, then a report is generated of failure 710. Should the attribute structure of the input specification be contained in, or be a subset of, the attribute structure of the initializing specification 706, then the attributes of the initializing specification are composed with the attributed values of the input specification, that is, the attribute values of the input specification are substituted as values for the attribute variables of the input specification 707. Should the constraints of the input specification be true after substitution of the attribute values of the input specification are substituted as values for the attribute variables of the initializing specification, then the input specification is said to be satisfied and such input specifications are said to satisfy the IoT search function or the IoT data quality policy as represented by the initializing specification 711. Should one or more of the constraints of the input specification be false after substitution of the attribute values of the input specification are substituted as values for the attribute variables of the initializing specification, then a report is generated of failure 710. Finally, the IoT specification obtained as above is assigned an ID 708 and the assigned ID is associated with the IoT List of the user 709.

It will be understood that each block of the flowchart illustrations, and combinations of blocks in the flowchart illustrations, can be implemented by computer program instructions. These computer program instructions may be provided to a processor or other programmable data processing apparatus to produce a machine, such that the instructions which execute on the processor or other programmable data processing apparatus create means for implementing the functions specified in the flowchart block or blocks. These computer program instructions may also be stored in a computer-readable memory or storage medium that can direct a processor or other programmable data processing apparatus to function in a particular manner, such that the instructions stored in the computer-readable memory or storage medium produce an article of manufacture including instruction means which implement the functions specified in the flowchart block or blocks.

Accordingly, blocks of the flowchart illustration support combinations of means for performing the specified functions, combinations of steps for performing the specified functions and program instruction means for performing the specified functions. It will also be understood that each block of the flowchart illustration, and combinations of blocks in the flowchart illustration, can be implemented by special purpose hardware-based computer systems which perform the specified functions or steps, or by combinations of special purpose hardware and computer instructions.

The characteristic information of an IoT is assessed using the method describe in FIG. 7 and the specifications of one or more IoT data quality policies to identify violations of one or more IoT data quality policies. A data quality policy is an IoT specification and is said to be satisfied if there are no failures as determined by the Characteristic Information Comparison 700. The User IoT List entries may then be updated based on identified violations, if any. Logs/reports of the violations may be generated and transmitted to the client IoT computing device and/or a data quality monitoring computing device.

Based on the assessment using a Machine Learning Module of the characteristic information of an IoT relative to a data quality policy using the method describe in FIG. 7 the system generates a report to the user and accepts further information from the user on the basis of the report which allows the system to propose a solutions and if so configured by a user to implement a solution that includes modification of the IoT device or system to improve the function or accuracy of the system.

It will be understood that each block of the flowchart illustrations, and combinations of blocks in the flowchart illustrations, can be implemented by computer program instructions. These computer program instructions may be provided to a processor or other programmable data processing apparatus to produce a machine, such that the instructions which execute on the processor or other programmable data processing apparatus create means for implementing the functions specified in the flowchart block or blocks. These computer program instructions may also be stored in a computer-readable memory or storage medium that can direct a processor or other programmable data processing apparatus to function in a particular manner, such that the instructions stored in the computer-readable memory or storage medium produce an article of manufacture including instruction means which implement the functions specified in the flowchart block or blocks.

Accordingly, blocks of the flowchart illustration support combinations of means for performing the specified functions, combinations of steps for performing the specified functions and program instruction means for performing the specified functions. It will also be understood that each block of the flowchart illustration, and combinations of blocks in the flowchart illustration, can be implemented by special purpose hardware-based computer systems which perform the specified functions or steps, or by combinations of special purpose hardware and computer instructions.

The characteristic information of an IoT is assessed using data quality policies to identify violations of the data quality policies, if any. The User IoT List entries may then be updated based on identified violations. Logs/reports of the violations may be generated and transmitted to the client IoT computing device and/or a data quality monitoring computing device and the operation terminates.

Thus, the present embodiments provide a mechanism for searching an IoT client, across a network connection, for IoT and IoT data. Based on the results of the search, data quality policies may be applied to determine if the IoT data of the IoT are in violation of data quality policies and to determine if IoT data are being maintained on the IoT client in accordance with established data quality policies. Any violations identified may be reported to a data quality monitor and/or to the user of the IoT client along with suggested solutions for bringing the IoT client into compliance with the established data quality policies. In this way, breaches of data quality policy may be quickly and easily identified in a network of IoT clients and solutions offered for ensuring the quality of IoT data.

It is important to note that while the present embodiments has been described in the context of a fully functioning data processing system, those of ordinary skill in the art will appreciate that the processes of the present embodiments are capable of being distributed in the form of a computer readable medium of instructions and a variety of forms and that the present embodiments applies equally regardless of the particular type of signal bearing media actually used to carry out the distribution. Examples of computer readable media include recordable-type media, such as a floppy disk, a hard disk drive, a RAM, CD-ROMs, DVD-ROMs, and transmission-type media, such as digital and analog communications links, wired or wireless communications links using transmission forms, such as, for example, radio frequency and light wave transmissions. The computer readable media may take the form of coded formats that are decoded for actual use in a particular data processing system.

While the embodiments has been described in conjunction with specific embodiments, it is evident that many alternatives, modifications, and variations will be apparent to those skilled in the art in light of the foregoing description. Accordingly, the present embodiments attempt to embrace all such alternatives, modifications, and variations that fall within the spirit and scope of the appended claims. Accordingly, the specification and drawings are to be regarded in an illustrative rather than a restrictive sense. Throughout this specification and the drawings and Figures associated with this specification, numerical labels of previously shown or discussed features may be reused in another drawing Figure to indicate similar features. It is also understood that the phraseology or terminology employed herein is for the purpose of description and not of limitation. It is to be understood that the description above contains many specifications, these should not be construed as limiting the scope of the embodiments but as merely providing illustrations of some of the personally preferred embodiments.

We claim:

1. A method for an Internet of Things (IoT) system and device, comprising:

exchanging information with one or more IoT objects;

creating domain-specific computer-readable languages to express constraints on attributes of the IoT information;

creating domain-specific computer-readable languages to express constraints on computer-readable names for the attributes of the IoT information, wherein the attributes of the IoT information include temperature, air quality, and humidity, in the domains of energy, automated transportation, building and facility management, supply chain, and healthcare;

creating domain-specific computer-readable languages to express constraints on computer-readable names for the attributes of the IoT information, wherein the constraints on the computer-readable names for the attributes of the IoT information include upper and lower bounds on temperature values;

creating a composition of constraints on the IoT information also known as a specification of the IoT information;

creating a composition of one or more specifications of IoT information for a purpose or an objective of searching over IoT specifications, also known as search rules;

creating a composition of two or more specifications of IoT information for a purpose or an objective of obtaining a specification of IoT information that results from compositions of specifications of IoT information, also known as IoT information composition;

creating IoT specifications in a domain-specific language for purposes of comparing the IoT information of two or more IoT by means of comparing the respective IoT specifications by means of logical relation between constraints of the respective IoT specifications;

wherein two or more IoT specifications are compared, and wherein when the comparison of the two or more IoT specifications is determined to be equivalent, incomparable, or a first IoT specification is logically implied by a second IoT specification, performing additional steps including:

determining an outcome of a comparison of IoT specifications is implicitly and explicitly associated with one or more pending actions, including determination of differences in values of CI of the IoT specifications;

employing one or more machine learning (ML) models to generate one or more risk assessment values that relate to the comparison of the two or more IoT specifications or to predict an evolution of IoT data over a time interval using machine learning and displaying to a user results of the comparison of the two or more IoT specifications, including one or more comparison outcomes, and one or more predicted risk assessment values that relate to the comparison of the two or more IoT specifications or to the predicted evolution of the IoT data over the time interval using machine learning; and employing in one implementation relating to healthcare a global positioning systems (GPS) device to provide geo-location information of personal communication devices in order to assess compliance with social distancing requirements or determine one or more risk values for a display to the user, including clustering of persons within a given distance of a designated person and predicting risk factors associated with a transmission associated with a movement of infected persons;

wherein the geo-location information of the personal communication devices is employed to select one or more spaces of an enclosed structure for inclusion in one or more of a document, a user interface, or a report that is used to update a display of the predicted risk factors associated with the transmission associated with the movement of the infected persons to the user.

* * * * *